(12) United States Patent
Edwards

(10) Patent No.: US 9,375,377 B1
(45) Date of Patent: Jun. 28, 2016

(54) HANDS-FREE CRUTCH ASSEMBLY

(71) Applicant: Amanda Marie Edwards, Jacksonville, FL (US)

(72) Inventor: Amanda Marie Edwards, Jacksonville, FL (US)

( * ) Notice: Subject to any disclaimer, the term of this patent is extended or adjusted under 35 U.S.C. 154(b) by 784 days.

(21) Appl. No.: 13/680,529

(22) Filed: Nov. 19, 2012

Related U.S. Application Data

(60) Provisional application No. 61/561,878, filed on Nov. 20, 2011.

(51) Int. Cl.
*A61F 5/00* (2006.01)
*A61H 3/00* (2006.01)

(52) U.S. Cl.
CPC .................................. *A61H 3/00* (2013.01)

(58) Field of Classification Search
CPC ....... A61F 5/00; A61F 5/0111; A61F 5/0126; A61F 5/0102; A61F 5/0195; A61F 2005/0132; A61F 2005/0146; A61F 2005/0169; A61F 2005/0181; A61H 3/00; A61H 3/02; A61H 3/0277; A61H 2003/0211; A61H 2003/0216; A61H 2003/005; A61H 2003/007
USPC ........ 601/5, 23, 24, 27, 33, 34, 35; 602/5, 16, 602/19, 23–29, 32, 36; 135/65, 66, 67, 69, 135/73, 74, 75, 82, 84
See application file for complete search history.

(56) References Cited

U.S. PATENT DOCUMENTS

| | | | | |
|---|---|---|---|---|
| 6,666,796 B1 * | 12/2003 | MacCready, Jr. | ..... | A61F 5/0102 135/65 |
| 6,997,891 B1 * | 2/2006 | Vecsey | ................. | A61F 5/0195 602/10 |
| 7,303,537 B1 * | 12/2007 | Snyder | ...................... | A61F 3/00 135/68 |
| 2010/0174219 A1 * | 7/2010 | Franke | .................. | A61F 5/0111 602/16 |

* cited by examiner

*Primary Examiner* — Quang D Thanh
(74) *Attorney, Agent, or Firm* — Allen Dyer Doppelt Milbrath & Gilchrist

(57) ABSTRACT

A hands-free crutch assembly allows a user's foot to float suspended over an artificial foot, while transferring at least a portion of the walking load to the upper leg and permitting more natural knee flexion and extension while walking.

19 Claims, 2 Drawing Sheets

HANDS-FREE CRUTCH ASSEMBLY

CROSS-REFERENCE TO RELATED APPLICATION

This application claims the benefit of U.S. Provisional Patent Application Ser. No. 61/561,878 filed on Nov. 20, 2011, the contents of which are herein incorporated by reference in their entirety.

FIELD OF THE INVENTION

The present invention relates to crutches, and more particularly, to hands-free crutches.

BACKGROUND OF THE INVENTION

In the case of injuries to the ankle, foot or toe, rather than a conventional crutch that requires employment of the user's arm and hand, an alternative option is a "hands-free" crutch that attaches directing to the affected leg. The hands-free crutch keeps pressure off of the ankle, foot and toe by holding it, in various manners, above the foot of the attached crutch, and as the name suggests, enjoys the advantage of freeing the user's hand for other activities while walking.

U.S. Pat. No. 5,178,595 is an example of a more highly developed version of the most basic hands-free crutch (i.e., the peg leg). Essentially, the user's knee is immobilized in a bent position and the user must swing the leg and attached crutch from the hip in order to walk. Another example of a hands-free crutch can be seen in U.S. Pat. No. 6,997,891. This hands-free crutch attaches only to the lower leg, thus allowing the leg to bend at the knee during walking, and consequently allowing the user to exercise the muscles associated with this movement. However, significant force is applied to the lower leg, and particularly to the patellar tendon, when walking. While hands-free crutches of these types have been useful, further improvements are possible.

SUMMARY OF THE INVENTION

In view of the foregoing, it is an object of the present invention to provide an improved hands-free crutch assembly. According to an embodiment of the present invention, a hands-free crutch assembly has a support brace for releasable attachment to a leg of a user, at least one pivot support mechanism attached to the support brace, at least one foot extension connected to the lower leg brace portion and extending downwardly therefrom, and a foot connected to a lower end of the of the at least one foot extension.

The support brace includes an upper leg brace portion releasably connectable along an upper leg of the user, and a lower leg brace portion releasably connectable along a lower leg of the user. At least one brace hinge connects a lower end of the upper leg brace portion to an upper end of the lower leg brace portion, and allows pivotable motion therebetween along a pivot axis.

The at least one pivot support mechanism extends between the upper and lower leg brace portions and includes a curved track extending rearwardly of the support brace along an arc coaxial with the pivot axis, and a carriage slidable on the curved track.

According to a method aspect, a method of using the hands-free crutch assembly includes attaching the support brace to a leg of a user, the upper leg brace portion being connected above the knee of the user and the lower leg brace portion being connected below the knee, with the pivot axis of the at least one brace hinge between the upper and lower leg brace portions.

The hands-free crutch assembly is walked with such that the foot of the user floats above the foot of the hands-free crutch assembly. Force from the foot of the crutch assembly is transferred to the support brace via the at least one foot extension extending between the foot of the hands-free crutch assembly to the lower leg brace portion and the at least one pivot support mechanism extending between the lower leg brace portion and upper leg brace portion. The at least one brace hinge and the at least one pivot support mechanism allow flexion and extension of the knee during walking, while transferring at least a portion of the force experienced during walking to the upper leg.

These and other objects, aspects and advantages of the present invention will be better understood with reference to the drawings and following detailed description of preferred embodiments.

DETAILED DESCRIPTION OF PREFERRED EMBODIMENTS

Figure 1:
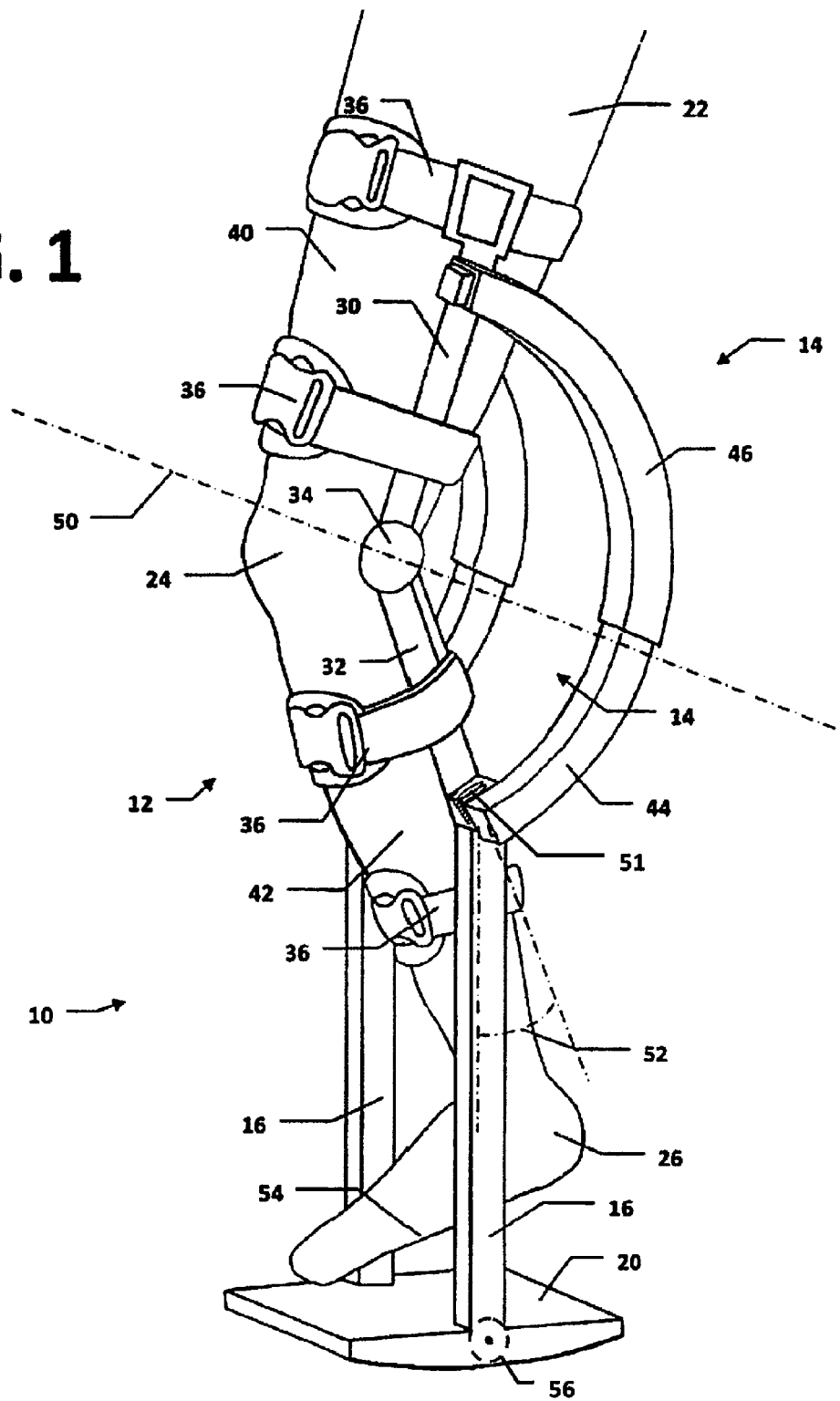
FIG. 1 is a perspective view of a hands-free crutch assembly, according to an embodiment of the present invention, worn on a leg.

Referring to FIG. 1, according to an embodiment of the present invention a hands-free crutch assembly 10 includes a support brace 12, lateral and medial pivot support mechanisms 14, lateral and medial foot extensions 16 and a foot 20. The support brace 12 connects to the leg 22 of a user above and below the knee 24, allowing the user's foot 26 to float suspended over the foot 20 of the assembly. The support brace 12 allows extension and flexion of the knee 24 while walking in the crutch assembly 10. The pivot support mechanisms 14 transfer a portion of the load from the foot 20 to the leg 22 above the knee 24, preventing excessive stress on the leg below the knee, particularly at the patellar tendon, and allowing a more natural walking gait.

Directional terms used herein, such as front and rear, lateral and medial, should be understood in the frame of reference of a standing human wearing the crutch assembly 10. Thus, an element that extends "rearwardly" of another element would do so when in that orientation, although the elements would not necessarily bear such relationship during other motions of the wearer.

The support brace 12 includes an upper leg brace portion 30 and a lower leg brace portion 32 connected by one or more brace hinges 34. The depicted brace 12 includes two hinges 34, although one is obscured by the knee 24. The hinges 34 allow the upper leg brace portion 30 to pivot relative to the lower leg brace portion 32. Advantageously, a plurality of straps 36, with associated buckles, pads and the like, are used to releasably secure the support brace 12 to the upper and lower legs 40, 42 of the user.

Other support braces can be used in connection with the hands-free crutch assembly of the present invention, including existing knee braces retrofitted for connection to the pivot support mechanisms 14 and foot extensions 16. The support brace used should connect securely above and below the knee 24 and allow flexion and extension thereof. An example of a suitable existing brace is the ROM-SS Knee Brace, sold by Townsend Design of Bakersfield, Calif.

Each pivot support mechanism 14 extends rearwardly of the support brace 12 between the upper and lower leg brace portions 30, 32 and includes a curved track 44 and a carriage 46 that is slidably guided thereon. The curved shape of the pivot support mechanisms 14 aid in the transference of some load to the upper leg 40, while still allowing relatively natural flexion and extension of the knee 24 while walking. To this end, the curved shape of the support mechanisms 14, and more particularly the tracks 44, define arcs that share a common axis 50 with the brace hinges 34. Likewise, the points at which the track 44 and carriage 46 attach to the support brace 12 should be equidistant from the brace hinge 34.

The track 44 is fixed to the lower leg brace portion 32 while the carriage 46 is fixed to the upper leg brace portion 30. While the track and carriage 44, 46 slide relative to each other along the arc defined thereby, preferably neither component moves relative to the respective brace portion 30, 32, to which it is affixed. It will be appreciated that the positions of the track 44, 46 could be reversed while maintaining their combined function, with the track 44 fixed to the upper leg brace portion 30 and the carriage 46 to the lower leg brace portion 32. Additionally, some degree of movement at the attachment points between the pivot support mechanism 14 and support brace 12 could be permitted to compensate for axis misalignment and the cam-like action of the knee joint which does not strictly rotate about the axis 50. Spring dampening could be employed at either or both of these joints (e.g., via a spring 51) to help manage this freedom of movement, as well as to absorb shocks that would otherwise be transmitted therethrough.

In the depicted embodiment, the carriage 46 includes an elongated, hollow curved member through which the track 44 passes. This elongated, curved carriage 46 advantageously offers a relatively large area over which force can be transferred, and which will permit force transference through the entire range of motion of the pivot support mechanism 14 (and consequently of the knee 24 during walking). However, other carriage shapes are possible. Likewise, the track 44 and carriage 46 are depicted as tubular members with square cross-sections, although the present invention is not necessarily limited to these shapes. For instance, tubular members with round or trapezoidal cross-sections, solid members, and/or members with flatter cross-sections could be employed. Additionally, various bearings could be interposed between the track 44 and carriage 46 to facilitate sliding movement.

The lateral and medial foot extensions 16 connect the foot 20 to the support brace 12 and the pivot support mechanisms 14. In the depicted embodiment, the upper end of each foot extension 16 connects to the lower leg support brace portion 32 at the same point as the lower end of the corresponding pivot support mechanism 14. Advantageously, the foot extensions 16 extend both downwardly and forwardly from the lower leg support brace portion 32. The extensions 16 extend forwardly at an angle 52 which is preferably selected to place the ball 54 of the user's foot 26 approximately in-line between the lateral and medial foot extensions 16. An angle 52 of approximately 20-30 degrees, and more preferably approximately 25 degrees, has been found generally suitable for this purpose.

The foot 20 interfaces with the ground during walking using the hands-free crutch assembly 10. The depicted foot 20 includes a rounded lower surface to facilitate smooth force transfer from heel strike to toe-off. The lower surface could be covered in a rubber or polymeric surface for increased traction, as well as cushioning. Other foot designs could be employed, however. Additionally, other mechanisms of attachment between the foot extensions 16 and foot 20 could be employed, such pivotable joints 56 (one shown) allowing increased ground contact with the foot 20 throughout each step. As with the pivot support mechanism, spring dampening could be employed at the joint(s) between the foot and the foot extension.

The present invention is not limited to particular materials of construction. In general, material selection should be made based on operational requirements, with strength, rigidity, lightness and durability during extended use typically being desirable qualities. Non-limiting examples of materials with advantageous strength, rigidity, weight and durability include steel, aluminum, titanium, carbon fiber and some plastics. Similarly, the present invention is not necessarily limited to particular means and/or mechanisms for connecting components together. For example, any of welding, bolting, pinning and riveting could be employed for a given joint, with the selection dictated by factors such as user preferences, manufacturing concerns and operability concerns relating to the associated joint.

Various mechanical components can be made so as to permit size adjustments. For example, the upper and lower leg brace portions 30, 32 can both incorporate joints allowing their lengths to be increased and decreased. Likewise, the foot extensions 16 can be lengthened and shortened. Also, for strength and even distribution of force, foot extensions, pivot support mechanisms and hinges are provided on both lateral and medial sides of the leg 22 in the depicted embodiment. However, depending on operational requirements and materials used, some or all of these components could be confined to a single side.

Figure 2:
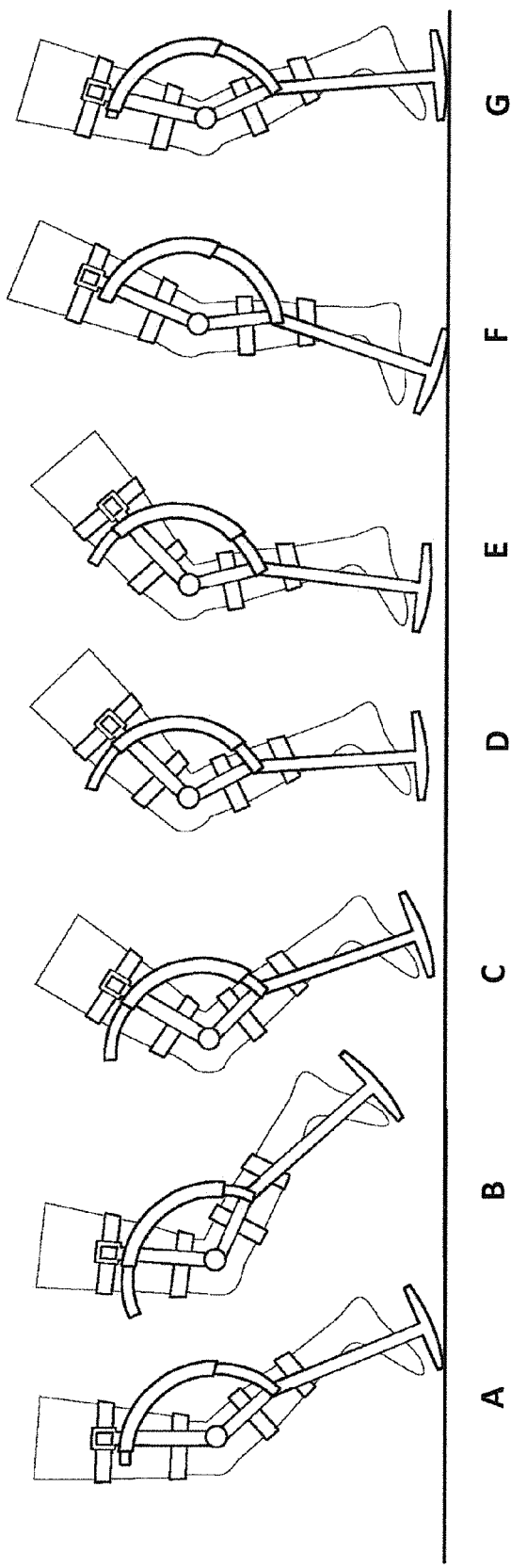
FIG. 2 is a time-lapsed sequence of side views of the hands-free crutch assembly and leg of FIG. 1, during walking.

Referring to FIG. 2, the operation of the hands-free crutch assembly 10 during a walking gait is shown at time-lapsed positions A-G. At position A toe-off is occurring (at positions A-F, the user's other foot would be in at least partial contact with the ground). In position B, the leg and crutch-assembly reach the pre-swing position. The leg and crutch assembly move through the swing phase in positions C-E, with initial swing (position C), midswing (position D) and terminal swing (position E). Heel strike occurs at position F, and transitions to the midstance position at position G. The leg and crutch assembly then return to position A and the gait cycle repeats.

The foregoing embodiments are provided for illustrative and descriptive purposes; the present invention is not necessarily limited thereto. Rather, those skilled in the art will appreciate that various modification, as well as adaptations to particular circumstances will fall within the scope of the invention herein shown and described, and of the claims appended hereto.

What is claimed is:

1. A hands-free crutch assembly comprising:
   a support brace for releasable attachment to a leg of a user including:
      an upper leg brace portion releasably connectable along an upper leg of the user;
      a lower leg brace portion releasably connectable along a lower leg of the user; and
      at least one brace hinge connected to a lower end of the upper leg brace portion and an upper end of the lower leg brace portion and allowing pivotable motion therebetween along a pivot axis;
   at least one pivot support mechanism extending between the upper and lower leg brace portions including:
      a curved track extending rearwardly of the support brace along an arc coaxial with the pivot axis; and a carriage slidable on the curved track;
at least one foot extension connected to the lower leg brace portion and extending downwardly therefrom; and
a foot of the hands-free crutch assembly connected to a lower end of the at least one foot extension.

2. The hands-free crutch assembly of claim 1, wherein the brace support includes a plurality of straps by which the upper and lower leg brace portions are releasably connectable to the upper and lower leg of the user.

3. The hands-free crutch assembly of claim 1, wherein the upper and lower leg brace portions each include lateral and medial sides.

4. The hands-free crutch assembly of claim 3, wherein the at least one brace hinge includes lateral and medial hinges respectively connecting the lateral and medial sides of the upper and lower leg brace portions.

5. The hands-free crutch assembly of claim 3, wherein the at least one pivot support mechanism comprises lateral and medial pivot supports extending between the lateral and medial sides of the upper and lower leg brace portions.

6. The hands-free crutch assembly of claim 3, wherein the at least one foot extension includes lateral and medial foot extensions extending downwardly from the lateral and medial sides of the lower leg brace portion and connecting lateral and medial sides of the foot of the hands-free crutch assembly.

7. The hands-free crutch assembly of claim 3, wherein the at least one foot extension extends downwardly and forwardly of the lower leg brace portion.

8. The hands-free crutch assembly of claim 7, wherein the at least one foot extension extends forwardly of the lower leg brace portion at an angle such that, with the user's leg secured in the support brace, a ball of the foot of the secured leg will be in line with the at least one foot extension.

9. The hands-free crutch assembly of claim 7, wherein the at least one foot extension extends forwardly of the lower leg brace portion at an angle of approximately 25 degrees.

10. The hands-free crutch assembly of claim 1, wherein the carriage includes a complementary elongated curved member riding on the curved track.

11. The hands-free crutch assembly of claim 1, wherein the at least one foot extension connects directly to a lower end of the at least one pivot support mechanism.

12. The hands-free crutch assembly of claim 1, wherein freedom of motion is permitted between the at least one pivot support mechanism and the support brace.

13. The hands-free crutch assembly of claim 12, wherein the freedom of motion is spring dampened.

14. The hands-free crutch assembly of claim 1, wherein freedom of motion is permitted between the at least one foot extension and the foot of the hands-free crutch assembly.

15. The hands-free crutch assembly of claim 14, wherein the freedom of motion is spring dampened.

16. A hands-free crutch assembly comprising:
a support brace for releasable attachment to a leg of a user including:
an upper leg brace portion releasably connectable along an upper leg of the user;
a lower leg brace portion releasably connectable along a lower leg of the user; and
lateral and medial brace hinges connected to a lower end of the upper leg brace portion and an upper end of the lower leg brace portion and allowing pivotable motion therebetween along a common pivot axis;
lateral and medial pivot support mechanisms extending between the upper and lower leg brace portions, each support mechanism including:
a curved track extending rearwardly of the support brace along an arc coaxial with the common pivot axis; and
a carriage slidable on the curved track;
lateral and medial foot extensions connected to the lower leg brace portion and extending downwardly and forwardly therefrom; and
a foot of the hands-free crutch assembly connected to lower ends of the lateral and medial foot extensions.

17. The hands-free crutch assembly of claim 16, wherein the lateral and medial foot extensions each extend forwardly of the lower leg brace portion at an angle such that, with the user's leg secured in the support brace, a ball of the foot of the secured leg will be in line between the lateral and medial foot extensions.

18. The hands-free crutch assembly of claim 16, wherein the carriage of each pivot support mechanism includes a hollow curved member through which the curved track passes.

19. The hands-free crutch assembly of claim 16, wherein the lateral and median foot extensions respectively connect directly to lower ends of the lateral and medial pivot support mechanisms.

\* \* \* \* \*